(12) United States Patent
Levy et al.

(10) Patent No.: US 9,510,813 B2
(45) Date of Patent: Dec. 6, 2016

(54) MEDICAL DEVICE

(75) Inventors: Arie Levy, Ramat-Gan (IL); Ofek Levin, Moshav Amirim (IL)

(73) Assignee: Covidien LP, Mansfield, MA (US)

(*) Notice: Subject to any disclaimer, the term of this patent is extended or adjusted under 35 U.S.C. 154(b) by 233 days.

(21) Appl. No.: 13/525,791

(22) Filed: Jun. 18, 2012

(65) Prior Publication Data

US 2013/0217974 A1 Aug. 22, 2013

Related U.S. Application Data

(63) Continuation of application No. PCT/IB2010/003400, filed on Dec. 14, 2010.

(60) Provisional application No. 61/290,215, filed on Dec. 27, 2009.

(51) Int. Cl.
*A61B 1/32* (2006.01)
*A61B 17/02* (2006.01)
*A61B 17/34* (2006.01)
*A61M 25/06* (2006.01)

(52) U.S. Cl.
CPC ....... *A61B 17/0218* (2013.01); *A61B 17/3417* (2013.01); *A61B 17/3421* (2013.01); *A61M 25/0668* (2013.01); *A61B 17/3462* (2013.01); *A61B 2017/349* (2013.01)

(58) Field of Classification Search
CPC ....... A61B 1/313; A61B 1/32; A61B 17/3462; A61B 2017/3464; A61B 2017/3466
USPC .............................. 600/201–246; 604/167.06
See application file for complete search history.

(56) References Cited

U.S. PATENT DOCUMENTS

| 5,755,693 A | * | 5/1998 | Walker | A61M 25/0668 604/160 |
| 6,786,888 B1 | | 9/2004 | Zadno-Azizi et al. | |
| 6,966,896 B2 | * | 11/2005 | Kurth et al. | 604/167.06 |
| 7,582,070 B2 | * | 9/2009 | Goode | A61M 39/06 604/160 |
| 8,371,555 B2 | * | 2/2013 | Rickerd | A61M 39/0606 251/367 |
| 8,485,970 B2 | * | 7/2013 | Widenhouse et al. | 600/201 |
| 2003/0195472 A1 | | 10/2003 | Green et al. | |
| 2004/0054330 A1 | | 3/2004 | Kurth et al. | |
| 2005/0228346 A1 | | 10/2005 | Goode et al. | |
| 2007/0123816 A1 | | 5/2007 | Zhu et al. | |

(Continued)

FOREIGN PATENT DOCUMENTS

EP 0645982 4/1995
WO 2010/132608 A2 11/2010

OTHER PUBLICATIONS

International Search Report for PCT/IB2010/003400 date of completion is Jun. 1, 2011 (2 pages).

(Continued)

*Primary Examiner* — Ellen C Hammond
*Assistant Examiner* — Christina Negrellirodrigue (57) ABSTRACT

This invention generally relates to a medical device assembly for facilitating a sealed working channel into a pressurized body cavity, and methods of use thereof. In certain embodiments, devices of the invention include a hollow body that is splittable along its length and being configured to move between an open configuration for operably coupling with a surgical instrument and a closed configuration, in which in the closed configuration, the device provides a seal that prevents gas leakage from an incision site of a body cavity while the instrument is in the body cavity.

19 Claims, 6 Drawing Sheets

(56) References Cited

U.S. PATENT DOCUMENTS

2008/0262527 A1 10/2008 Eder et al.
2009/0062832 A1 3/2009 Griffith et al.
2009/0204081 A1 8/2009 Whittaker et al.

OTHER PUBLICATIONS

Extended European Search Report from Application No. EP 10838776.2-1659 dated Jul. 2, 2015.

* cited by examiner

MEDICAL DEVICE

CROSS-REFERENCE TO RELATED APPLICATIONS

This application is a continuation application claiming the benefit of, and priority to, International Application Number PCT/IB2010/003400, filed on Dec. 14, 2010, which claims the benefit of, and priority to, U.S. Provisional Patent Application No. 61/290,215, filed on Dec. 27, 2009.

FIELD OF THE INVENTION

This invention generally relates to medical devices for facilitating a sealed working channel into a pressurized body cavity.

BACKGROUND OF THE INVENTION

Various medical procedures require that sealing access ports be provided for the introduction and removal of surgical tools, guide wires, catheters or other items into the cavity or vessel being operated upon. A sealing access port is necessary when the procedure is carried out in a region of higher pressure within the body that must be maintained at that pressure without allowing significant leakage. For example, in a laparoscopic procedure within the abdomen, carbon dioxide gas is pumped into the abdomen to form an expanded or enlarged cavity within which the procedure may be carried out. As various tools are inserted and removed through the access ports, it is advantageous that the ports seal substantially fluid-tight to maintain the gas pressure within the cavity and keep it inflated.

Access ports currently provide a seal that prevents leakage when there is no tool inserted through the port. However, when a tool or other item is inserted through the port and manipulated, the seals as currently configured cannot maintain sufficient integrity to prevent significant leakage. It would be advantageous to provide an access port or an introducer that provides an adequate fluid-tight seal under all conditions of use, e.g., when a tool or item extends through the port into the cavity or vessel which is the subject of the procedure.

SUMMARY OF THE INVENTION

This invention generally relates to medical devices for facilitating a sealed working channel into a pressurized body cavity. Devices of the invention are configured to wrap around a surgical tool after the tool has been inserted into a body cavity and are configured to provide a sealed channel that prevents gas leakage from the body cavity while still allowing an operator to use a surgical instrument within the body cavity.

Devices of the invention include a hollow body that is splittable along its length and being configured to move between an open configuration for operably coupling with a surgical instrument and a closed configuration, in which in the closed configuration, the device provides a seal that prevents gas leakage from an incision site of a body cavity while the instrument is in the body cavity.

The body may include a first portion, and a second portion, wherein the first and second portion are hingedly connected. An inner surface of the first and second portion may include a gasket. The gasket provides for sealing of the channel when the device is in a closed position and wrapped around the surgical instrument. Devices of the invention may include a locking mechanism. A proximal portion of the device may be configured for insertion into the incision site of the body cavity. The device may also include a stopping mechanism that prevents insertion of a distal portion of the device into the incision site of the body cavity. Alternatively, a proximal portion of the device is configured to provide a gas-tight seal with the tissue surrounding the incision site.

The surgical instrument may be any surgical instrument known in the art that is designed for insertion into a body cavity. In certain embodiments, the surgical instrument is an instrument that is used in a laproscopic procedure. In other embodiments, the surgical instrument is an instrument that is used to laproscopically repair a hernia. In particular embodiments, the surgical instrument is a mesh deployment device, such as a hernia mesh deployment device. Exemplary mesh deployment devices are shown in PCT/IL2009/000188 and PCT/IL2009/000985, the content of each of which is incorporated by reference herein in its entirety.

Another aspect of the invention, provides a device for facilitating creation of a sealed channel into a body cavity including a hollow body configured to interact with a surgical instrument, the body being splittable along its length and including a first portion and a second portion that are hingedly connected, in which the body has an open configuration and a closed configuration, and a gasket located along an inner surface of the first and second portion.

Another aspect of the invention provides methods for providing a sealed channel into an incision site of a body cavity. Those methods involve creating an incision site in a body cavity, inserting a surgical instrument into the body cavity, coupling a device for facilitating the creation of a sealed channel into a body cavity to the instrument, and using the device to provide a seal that prevents gas leakage from the incision site in the body cavity while the instrument is in the body cavity.

BRIEF DESCRIPTION OF THE DRAWINGS

In order to understand the invention and to see how it may be implemented in practice, a plurality of embodiments will now be described, by way of non-limiting example only, with reference to the accompanying drawings, in which FIGS. 1A-1D illustrating a preferred embodiment of the present invention.

DETAIL DESCRIPTION OF THE SPECIFIC EMBODIMENTS

The present invention provides a splittable cannula (SC) in which the SC is adapted to envelope a shaft of a laparoscopic surgical tool without having to thread the surgical tool through the SC; Furthermore, once the SC is fitted (i.e., enveloped) onto the laparoscopic surgical tool, the SC is adapted to substantial seal the body cavity from the outside environment, such that major gas leakage from the body cavity is prevented.

It should be emphasized that some of the major advantages of the present invention, with respect to the prior art, is the ability to insert tools and implants through an incision made by a standard cannula-trocar assembly in which the tools/implants are too large to pass through the cannula.

It is one object of the present invention to provide a splittable cannula (SC) adapted to envelope a shaft of a surgical tool; the surgical tool comprising a distal portion and proximal portion interconnected via the shaft; the distal portion is adapted to be at least partially introduced into a pressurized body cavity during a minimal invasive surgery through a standard cannula or an incision; the SC is characterized by at least two configurations: (i) an open configuration (OC) in which a gap W is obtained through which the shaft of the surgical tool can be inserted; and, (ii) a closed configuration (CC) in which the gap is minimized or eliminated such that the SC substantially envelopes the shaft of the surgical tool; in which (i) the enveloping is obtained without threading the surgical tool through the SC; and, (ii) the SC substantially prevents gas leakage from the body cavity through the incision.

It is another object of the present invention to provide the SC as defined above, in which the SC comprises at least two sections 101 hinge-like coupled together.

It is another object of the present invention to provide the SC as defined above, in which the two sections can rotate one with respect to the other along a common edge which is substantially parallel to the main longitude axis of the SC.

It is another object of the present invention to provide the SC as defined above, in which the SC additionally comprising a locking portion which is adapted to maintain the SC at its the CC.

It is another object of the present invention to provide the SC as defined above, in which the locking portion comprising at least two locking sections located on the outer surface of the proximal portion of the SC; the two locking sections are adapted to be interlocked once they are pressed together.

It is another object of the present invention to provide the SC as defined above, in which the locking portion comprising a spring adapted to maintain the SC at its the CC.

It is another object of the present invention to provide the SC as defined above, in which the SC additionally comprising at least one penetration prevention section (PPS) located on the outer surface of the proximal portion of the SC, adapted to prevent complete penetration of the SC into the body; further in which the PPS is characterized by having a greater cross section area than the rest of the SC.

It is another object of the present invention to provide the SC as defined above, in which the SC additionally comprising at least one gasket adapted to substantially prevent gas leakage through the gap once the SC is at its the CC.

It is another object of the present invention to provide the SC as defined above, in which the SC additionally comprising a radial gasket located at the inner surface of the proximal portion of the SC; the radial gasket is adapted to prevent gas leakage through the interface between the shaft and the SC.

It is another object of the present invention to provide the SC as defined above, in which the radial gasket is characterized by having a C-shape.

It is another object of the present invention to provide the SC as defined above, in which the radial gasket is adapted to seal the cavity and prevent the gas leakage once the SC is at its the CC and the surgical tool is removed from the SC.

It is another object of the present invention to provide the SC as defined above, in which the radial gasket comprising at least two flexible leafs tiled with respect to the SC's inner surface and facing toward the distal portion of the SC.

It is another object of the present invention to provide the SC as defined above, in which the SC additionally comprising a slide prevention portion (SPP) located on at least a portion of the outer surface of the SC; further in which the SPP is adapted to prevent accidental sliding of the SC toward the proximal portion of the surgical tool during the surgery.

It is another object of the present invention to provide the SC as defined above, in which the distal edge of the SC is cone-like shaped for improving the insertion of the SC into the cavity.

It is another object of the present invention to provide the SC as defined above, in which the surgical tool is a hernia mesh deployment device.

It is another object of the present invention to provide a method for preventing gas leakage from a pressurized body cavity during a surgery. The method comprises steps selected from:

a. inserting a standard laparoscopic trocar into the patient's tissue trough an incision 203;
b. obtaining a laparoscopic surgical tool 204 having a main shaft;
c. removing the trocar from the patient's tissue;
d. inserting at least a portion of the tool 204 into the pressurized body cavity through the incision;
e. obtaining at least one splittable cannula (SC) adapted to envelope a shaft of, a surgical tool; the surgical tool is adapted to be at least partially introduced into a pressurized body cavity during a minimal invasive surgery through a standard cannula or an incision; the SC comprises at least two sections 101 hinge-like coupled together; the SC is characterized by at least two configurations: (i) an open configuration (OC) in which the two sections are apart to create a gap W through which the shaft of the surgical tool can be inserted; and, (ii) a closed configuration (CC) in which the gap is minimized or eliminated such that the SC substantially envelopes the shaft of the surgical tool; in which (i) the enveloping is obtained without threading the surgical tool through the SC; and, (ii) the SC substantially prevent gas leakage from the body cavity through the incision; the SC is provided in the open configuration;
f. inserting the shaft of the surgical tool into the SC through the gap W of the SC; and,
g. transforming the SC from the open configuration into the closed configuration, thereby enveloping of the shaft and preventing the gas leakage from the pressurized body cavity.

It is another object of the present invention to provide the method as defined above, additionally comprising step of sliding the SC along the shaft such that at least a portion of the SC is inserted into the patient's tissue through the incision It is another object of the present invention to provide the method as defined above, additionally comprising step of selecting the surgical tool to be a hernia mesh deployment device.

It is another object of the present invention to provide the method as defined above, in which the step of transforming the SC from the open configuration into the closed configuration by rotating the two sections one with respect to the other along a common edge which is substantially parallel to the main longitude axis of the SC.

It is another object of the present invention to provide the method as defined above, additionally comprising step of providing the SC with a locking portion which is adapted to maintain the SC at its the CC.

It is another object of the present invention to provide the method as defined above, additionally comprising step of providing the locking portion with at least two locking sections located on the outer surface of the proximal portion of the SC; the two locking sections are adapted to be interlocked once they are pressed together.

It is another object of the present invention to provide the method as defined above, additionally comprising step of providing the SC with at least one penetration prevention section (PPS) located on the outer surface of the proximal portion of the SC; the PPS is characterized by having a greater cross section area than the rest of the SC.

It is another object of the present invention to provide the method as defined above, additionally comprising step of preventing complete penetration of the SC into the body.

It is another object of the present invention to provide the method as defined above, additionally comprising step of providing the SC with at least one gasket adapted to substantially prevent gas leakage through the gap once the SC is at its the CC.

It is another object of the present invention to provide the method as defined above, additionally comprising step of providing the SC with a radial gasket located at the inner surface of the proximal portion of the SC; the radial gasket is adapted to prevent gas leakage through the interface between the shaft and the SC.

It is still an object of the present invention to provide the method as defined above, in which the radial gasket is adapted to seal the cavity and prevent the gas leakage once the SC is at its the CC and the shaft is removed from the SC.

It is lastly an object of the present invention to provide the method as defined above, additionally comprising step of providing the SC with a slide prevention portion (SPP) located on at least a portion of the outer surface of the SC; further in which the SPP is adapted to prevent accidental sliding of the SC toward the proximal portion of the surgical tool during the surgery.

The term "Hernia" refers hereinafter to umbilical hernia, hiatal hernia, ventral hernia, postoperative hernia, epigastric hernia, spiegelian hernia, inguinal hernia and femoral hernia, generally any abdominal wall related hernia.

The term "mesh deployment system" refers hereinafter to any device adapted to deploy a mesh/patch during a hernia surgery.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components. The term "hinge like connection" can refer to a standard hinge or to a living hinge (i.e., a thin flexible hinge (flexure bearing) made from plastic that joins two rigid parts together while allowing them to bend along the line of the hinge).

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "pressurized body cavity" refers hereinafter to a body cavity (e.g. intraperitoneal cavity) which is insufflated by gas (e.g. $CO_2$) during a minimal invasive surgery.

Figure 1A:
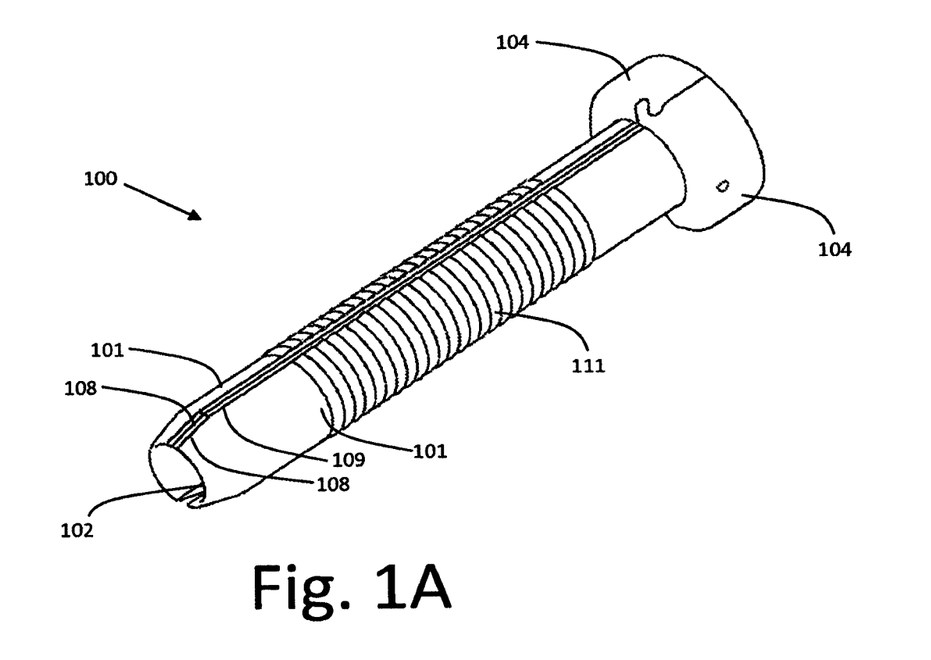

The term "closed configuration" refers hereinafter to the configuration of the SC 100 shown in FIG. 1A.

Figure 1B:
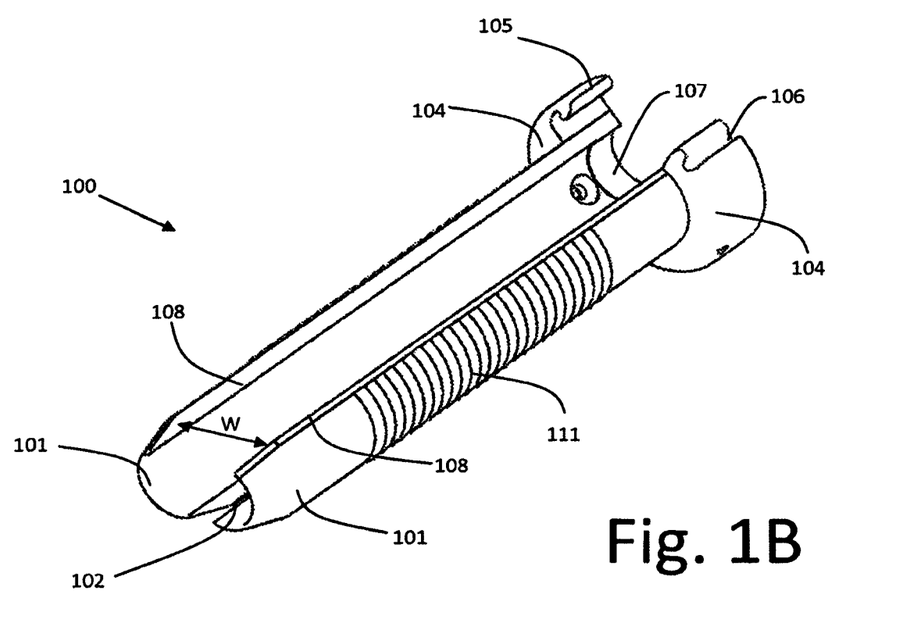
Figure 1C:
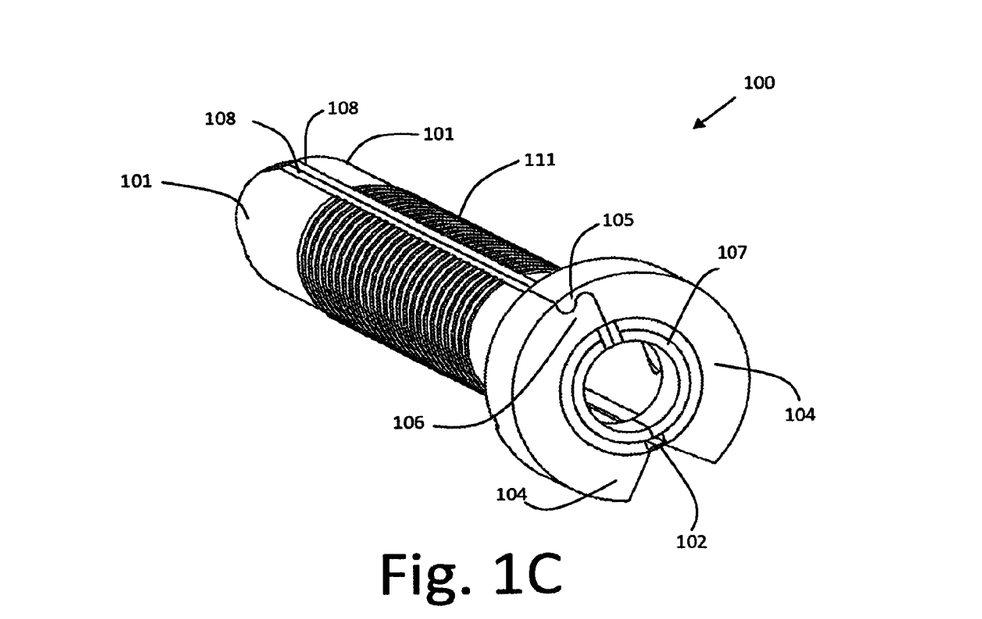
Figure 1D:
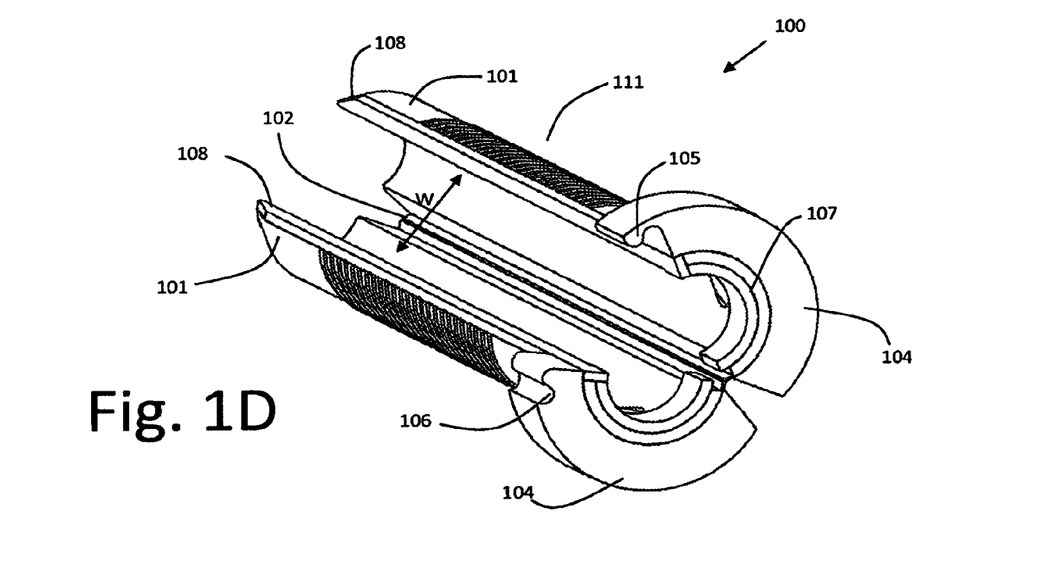

The term "open configuration" refers hereinafter to the configuration of the SC 100 shown in FIG. 1B.

Before explaining the figures, it should be understood that the invention is not limited in its application to the details of construction and the arrangement of the components set forth in the following description or illustrated in the drawings. The invention can be carried out in various ways.

Reference is now made to FIGS. 1A-1D illustrating a preferred embodiment of the present invention. According to that embodiment a splittable cannula (SC) 100 is provided. The SC 100 comprises two sections 101 connected to each another via a hinge 102 such that a movement of each of the sections relatively to each other is enabled around the hinge.

Hinge 102 can be either a living hinge on a conventional hinge. The SC 100 is characterized by two separate configurations: open configuration (OC) and closed configuration (CC). In the open configuration (FIG. 1B) the two sections 101 are positioned apart from each other such that a gap (W) is created between them through which a surgical tool shaft can be inserted. In the closed configuration (FIG. 1A) the portions 102 are substantially adjacent to one another such that the SC 100 can be regarded as a tube.

A locking section 104 is located at the outer surface of each section 101, such that the locking section 104 encircle the two sections 101. The locking section 104 is preferably positioned near the proximal end of the sections 101 (relative to the surgeon). The locking section 104 is adapted to hold the two sections 102 substantially adjacent to one another such that SC 100 is held at it's the CC.

According to one embodiment of the locking section 104, a locking hook 105 is positioned at one end of the locking section 104 and a locking socket 106 is positioned on the other end of the locking section 104. Once the two locking sections are pressed together, the locking hook 105 is pressed into the socket 106; thus, providing closure of the two portions 101 and the conversion of the SC 100 from the open configuration to the closed configuration. According to another embodiment of the locking section 104, the locking section 104 comprises a C shaped spring which holds the two sections 101 in contact with one another.

A penetration preventing section (PPS) is preferably positioned near the proximal end of the SC 100. The PPS is adapted to prevent the SC from fully penetrating into the patient's body during the surgery.

It should be noted that the SC 100 can partially introduced into the body cavity; however, it should not be fully introduced into the cavity.

The PPS is characterized by having larger cross section area than the rest of the SC 100 such that the SC 100 will not be able to pass through the incision. In a preferred embodiment the locking section 104 also functions as the PPS A radial gasket 107 is located at the proximal end of the SC 100. The gasket 107 is adapted to prevent gas leakage (i.e. radial sealing) through the gap between the shaft of a laparoscopic surgical tool and the inner surface of the SC 100. The radial sealing is obtained once SC 100 is at its the CC.

As disclosed above, gasket 107 is adapted to provide sealing so as to prevent gas leakage from the body cavity. This is done whilst still allowing reciprocal linear motion of the laparoscopic surgical tool's shaft inside SC 100 once the SC 100 at its CC (this is enabled since the gasket is soft and flexible material).

In one embodiment, gasket 107 is C-shaped (see FIGS. 1C-1D); according to this embodiment gasket 107 is preferably made of a soft and flexible material, e.g. foam rubber, silicon rubber.

In another embodiment, gasket 107 comprises a number of flexible leafs arranged radially and tilted with respect to the inner surface of the SC 100 such that once the SC is at its the CC and the shaft is removed the shape of the gasket 107 is transformed into a cone therefore preventing gas leakage from the body cavity and function as a valve; this feature will enable the use of the SC 100 as a standard laparoscopic cannula once it is its the CC According to another embodiment of the present invention, at least one linear gasket 108 is positioned along the main longitudinal axis of the SC 100, at the edge of at least one section 101. The gasket 108 is adapted to substantially prevent gas leakage along the interface between the two sections 101 once SC 100 is in its the CC.

A slide prevention portion (SPP) 111 is poisoned on a least a portion of the outer surface of the SC 100. The SPP 111 is adapted to prevent SC 100 from un deliberate slide of the SC 100 out of the patient's tissue during the surgery. The SPP provides friction such that unwanted movement is prevented. The unwanted movement is prevented by the SPP whilst still allowing insertion of the SC 100 into the patient's tissue.

The distal portion of SC 100 is conically shaped in order to allow the insertion of SC 100 into the patient's tissue once the SC 100 is in its closed configuration.

Figure 2A:
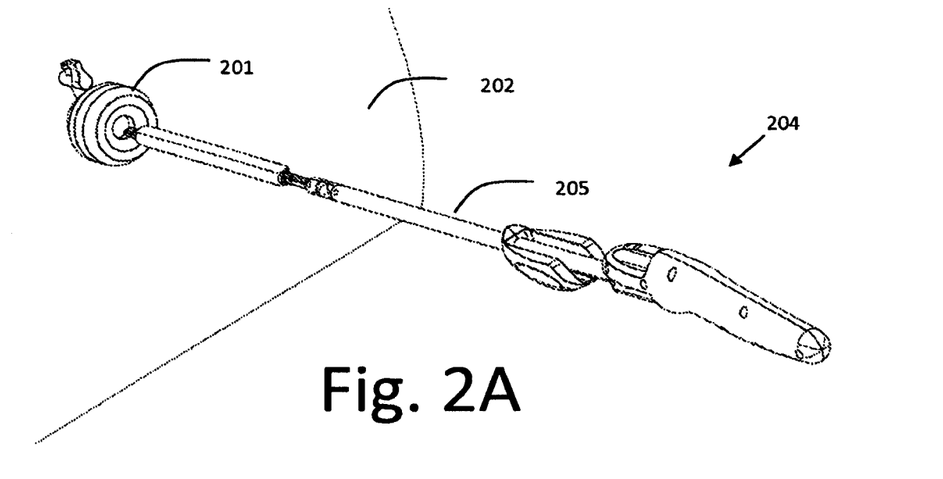
FIGS. 2A-2F illustrating a method utilizing the SC 100 during a laparoscopic surgery.
Figure 2B:
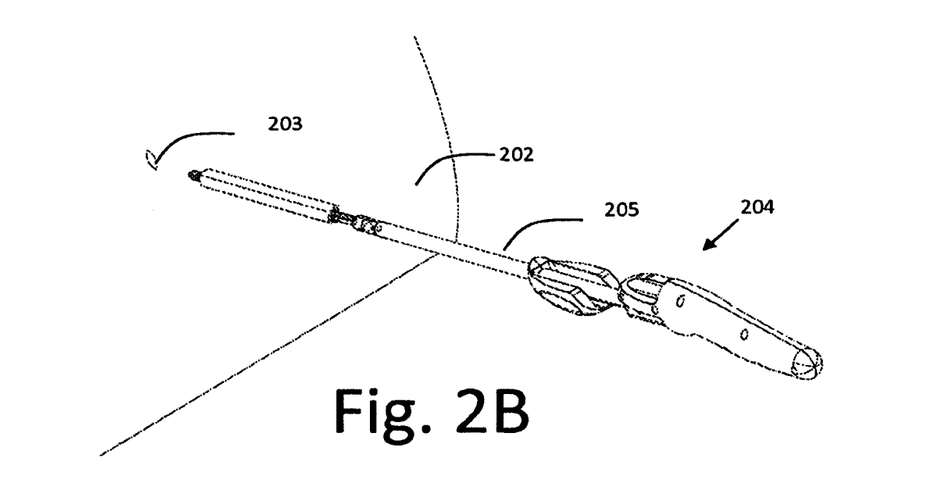
Figure 2C:
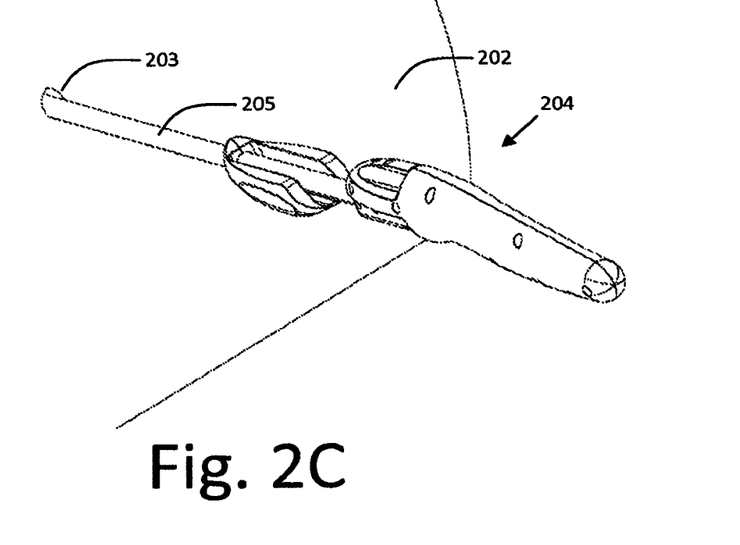
Figure 2D:
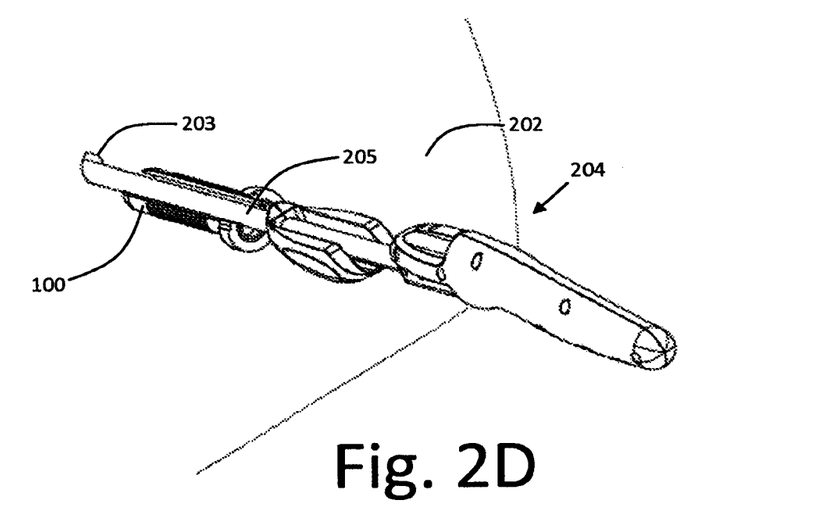
Figure 2E:
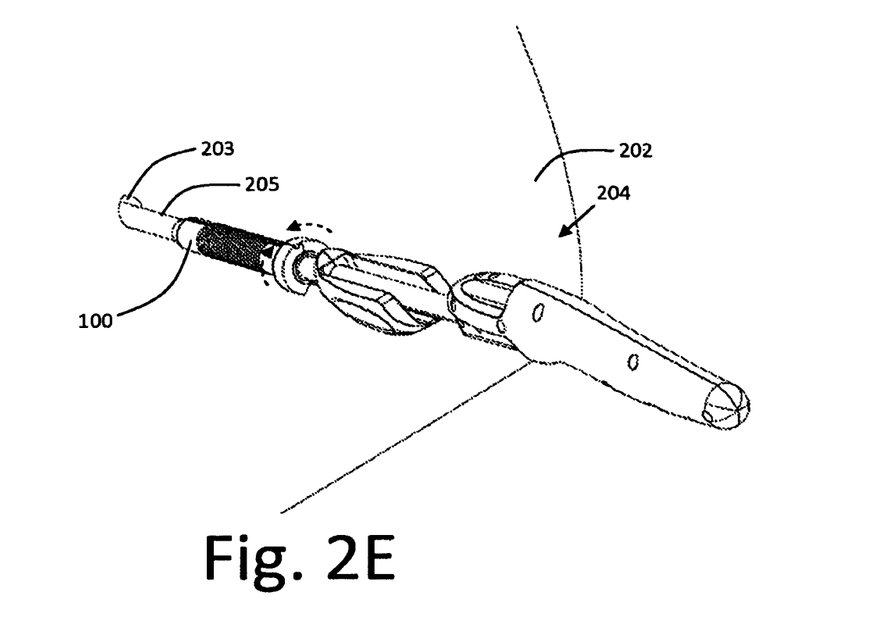
Figure 2F:
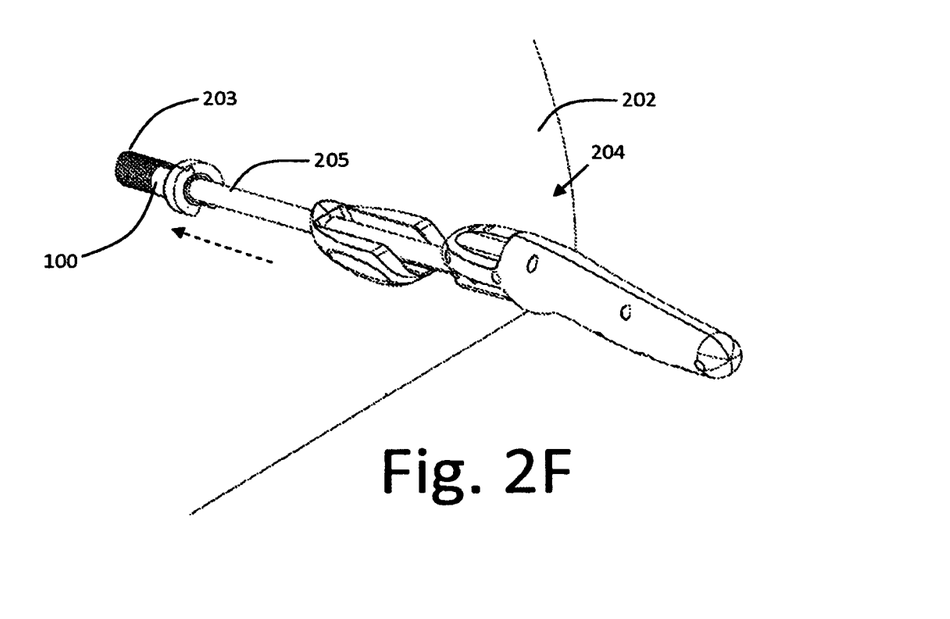

Reference is now made to FIGS. 2A-2F which describes a method utilizing the SC 100 (as described above) during a laparoscopic surgery. The method comprises steps selected inter alia from:

1. Inserting a standard laparoscopic trocar 201 into the patient's tissue 202 through an incision 203 and obtaining laparoscopic surgical tool 204 (FIG. 2A)
2. Removing the trocar 201 from the patient's tissue 202 (FIG. 2B).
3. Inserting at least a portion of the tool 204 into the patient's tissue 202 through the incision 203 (FIG. 2C).
4. Obtaining SC 100 in its open configuration.
5. Inserting shaft 205 of the tool 204 into the SC 100 through gap W (FIG. 2D).
6. Transforming the SC 100 from its the open configuration into its the closed configuration such that the SC 100 is enveloping the shaft 205 (FIG. 2E).
7. Sliding the SC 100 along the shaft 205 such that at least of apportion of the SC 100 is inserted into the patient's tissue 202 through incision 203 (FIG. 2F).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A device for facilitating creation of a sealed channel into a body cavity, the device comprising:
    a hollow body having first and second portions hingedly connected to each other, the hollow body splittable along its length and configured to move between an open configuration and a closed configuration, the hollow body defining a lumen extending between open proximal and distal ends in the closed configuration, the hollow body configured to sealingly engage a surgical instrument extending through the open proximal end of the hollow body to prevent gas leakage from a pressurized body cavity through the hollow body in the closed configuration and allowing gas leakage in the closed configuration in the absence of the surgical instrument; and
    a locking mechanism for holding the hollow body in the closed configuration, the locking mechanism having a spring that biases the hollow body toward the closed configuration.

2. The device according to claim 1, wherein the device further comprises at least one gasket.

3. The device according to claim 2, wherein the at least one gasket is a linear gasket.

4. The device according to claim 2, wherein the at least one gasket is a radial gasket.

5. The device according to claim 4, wherein the at least one gasket prevents gas leakage from the pressurized body cavity through the hollow body while still allowing movement of the surgical instrument extending through the hollow body.

6. The device according to claim 1, wherein a distal portion of the hollow body is configured for insertion into an incision site of the body cavity.

7. The device according to claim 1, further comprising a stopping mechanism configured to prevent insertion of a proximal portion of the device into an incision site of the body cavity.

8. The device according to claim 1, further comprising a slide prevent mechanism configured to prevent substantial movement of the device relative to a body wall during a surgical procedure.

9. A method for providing a sealed channel into a body cavity, the method comprising:
    coupling a device to a surgical instrument, the device including a hollow body with first and second portions hingedly connected to one another, the hollow body having open proximal and distal ends, the hollow body movable between an open configuration adapted to allow the device to receive the surgical instrument and a closed configuration to sealingly engage the surgical instrument extending through the open proximal end of the hollow body, the hollow body defining a passage extending between open proximal and distal ends in the closed configuration and allowing gas leakage in the closed configuration in the absence of the surgical instrument; and
    positioning the device with the surgical instrument coupled thereto such that the hollow body extends across a body wall with a distal portion of the surgical instrument extending into the body cavity, the hollow body being in the closed configuration sealingly engaging the surgical instrument thereby preventing gas leakage from the body cavity while the distal portion of the surgical instrument is positioned therein.

10. The method according to claim 9, further comprising positioning the distal portion of the surgical instrument within the body cavity prior to coupling the device to the surgical instrument.

11. A device for facilitating creation of a sealed channel into a body cavity, the device comprising:
    a hollow body having first and second portions hingedly connected to each other, the hollow body splittable along its length and configured to move between an open configuration and a closed configuration, the hollow body defining a lumen extending between open proximal and distal ends in the closed configuration, the hollow body configured to sealingly engage a surgical instrument extending through the open proximal end of the hollow body to prevent gas leakage from a pressurized body cavity through the hollow body in the closed configuration and allowing gas leakage in the closed configuration in the absence of the surgical instrument, wherein a distal portion of the hollow body is configured for insertion into an incision site of the body cavity; and a stopping mechanism configured to prevent insertion of a proximal portion of the device into the incision site of the body cavity, first and second portions of the stopping mechanism disposed on respective outer surfaces of the first and second portions of the hollow body and defining a diameter greater than a diameter of the hollow body in the closed configuration.

12. The device according to claim 11, wherein the device further comprises at least one gasket.

13. The device according to claim 12, wherein the at least one gasket is a linear gasket.

14. The device according to claim 12, wherein the at least one gasket is a radial gasket.

15. The device according to claim 14, wherein the at least one gasket prevents gas leakage from the pressurized body cavity through the hollow body while still allowing movement of the surgical instrument extending through the hollow body.

16. The device according to claim 11, further comprising a locking mechanism for holding the hollow body in the closed configuration.

17. The device according to claim 16, wherein the locking mechanism comprises a spring that biases the hollow body toward the closed configuration.

18. The device according to claim 16, wherein the stopping mechanism and the locking mechanism are unitarily formed.

19. The device according to claim 11, further comprising a slide prevent mechanism configured to prevent substantial movement of the device relative to a body wall during a surgical procedure.

* * * * *